United States Patent
Thorstenson et al.

(10) Patent No.: US 10,293,139 B2
(45) Date of Patent: May 21, 2019

(54) CATHETER AND METHOD OF MANUFACTURE

(71) Applicant: St. Jude Medical, Atrial Fibrillation Division, Inc., St. Paul, MN (US)

(72) Inventors: Chad A. Thorstenson, Andover, MN (US); James D. Savage, Port Jefferson Station, NY (US)

(73) Assignee: St. Jude Medical, Atrial Fibrillation Divison, Inc., St. Paul, MN (US)

( * ) Notice: Subject to any disclaimer, the term of this patent is extended or adjusted under 35 U.S.C. 154(b) by 211 days.

(21) Appl. No.: 14/978,719

(22) Filed: Dec. 22, 2015

(65) Prior Publication Data

US 2016/0114133 A1    Apr. 28, 2016

Related U.S. Application Data (63) Continuation of application No. 12/527,332, filed as application No. PCT/US2008/054149 on Feb. 15, 2008, now Pat. No. 9,254,374.

(60) Provisional application No. 60/901,344, filed on Feb. 15, 2007.

(51) Int. Cl.
| | |
|---|---|
| *A61M 25/00* | (2006.01) |
| *A61M 25/01* | (2006.01) |
| *A61M 25/06* | (2006.01) |
| *B29C 41/20* | (2006.01) |
| *B29L 31/00* | (2006.01) |

(52) U.S. Cl.
CPC .... *A61M 25/0147* (2013.01); *A61M 25/0012* (2013.01); *A61M 25/0053* (2013.01); *A61M 25/0662* (2013.01); *B29C 41/20* (2013.01); *A61M 25/0045* (2013.01); *B29L 2031/7542* (2013.01); *Y10T 156/10* (2015.01)

(58) Field of Classification Search
CPC ............ A61M 25/005; A61M 25/0053; A61M 2025/0081; A61M 25/0054; A61M 25/0662; A61M 25/104
USPC ... 604/96.01, 164.01, 523–532, 95.01–95.05
See application file for complete search history.

(56) References Cited

U.S. PATENT DOCUMENTS

| | | | |
|---|---|---|---|
| 5,329,923 A * | 7/1994 | Lundquist | .......... A61B 18/1492 600/373 |
| 5,531,721 A | 7/1996 | Pepin | |
| 5,702,373 A | 12/1997 | Samson | |
| 5,851,195 A * | 12/1998 | Gill | ....................... A61M 25/04 604/500 |
| 5,957,893 A | 9/1999 | Luther et al. | |
| 6,824,553 B1 | 11/2004 | Samson et al. | |
| 2004/0073158 A1 | 4/2004 | Shah et al. | |

(Continued)

OTHER PUBLICATIONS

International Search Report and Written Opinion for PCT/US2008/054149, dated Aug. 7, 2008.

*Primary Examiner* — Phillip A Gray (74) *Attorney, Agent, or Firm* — Wiley Rein LLP (57) ABSTRACT

The instant invention relates generally to introducer catheters used to help deliver catheters or other medical devices to locations within the human body. In particular, the instant invention relates to large diameter introducer catheters (introducer catheters with lumens greater than about 6 French) having increased strength, flexibility, and kink resistance. Introducer catheters according to the teachings herein may also include curved distal ends and flared (that is, funnel-like) transition sections within their lumens.

9 Claims, 9 Drawing Sheets

(56) References Cited

U.S. PATENT DOCUMENTS

| | | | |
|---|---|---|---|
| 2004/0087933 A1 | 5/2004 | Lee et al. | |
| 2004/0254422 A1* | 12/2004 | Singh | A61B 1/0008 600/160 |
| 2005/0272975 A1* | 12/2005 | McWeeney | A61B 1/00071 600/113 |

* cited by examiner

CATHETER AND METHOD OF MANUFACTURE

CROSS-REFERENCE TO RELATED APPLICATIONS

This application is a continuation of U.S. application Ser. No. 12/527,332, filed 14 Aug. 2009, now pending, which is a national stage application of international application no. PCT/US2008/054149, filed Feb. 15, 2008, now expired, which claims the benefit of U.S. provisional application No. 60/901,344, filed Feb. 15, 2007. Each of the foregoing is hereby incorporated by reference as though fully set forth herein.

BACKGROUND OF THE INVENTION a. Field of the Invention

The instant invention relates generally to catheters and to introducer catheters used to help deliver catheters or other medical devices to locations within the human body. In particular, the instant invention relates to catheters and introducer catheters having a torque transfer layer configured to provide increased strength, flexibility, and kink resistance.

b. Background Art

Catheters are used for an ever growing number of medical procedures. To name just a few examples, catheters are used for diagnostic, therapeutic, and ablative procedures. Typically, the physician manipulates the catheter through the patient's vasculature to the intended site, such as a site within the patient's heart. The catheter typically carries one or more electrodes or other diagnostic or therapeutic devices, which may be used for ablation, diagnosis, cardiac mapping, or the like.

It is known that, to facilitate placement of the diagnostic or therapeutic catheter at a location of interest within the patient, it may be introduced through another catheter, commonly known as a "guiding catheter" or "introducer catheter," and the terms will be used interchangeably herein. Generally speaking, an introducer catheter is a tube having a high degree of directional control that is used to place other catheters, which may have little or no directional control, into specific areas of the patient's body.

In the field of cardiac ablation, for example, introducer catheters may be used to negotiate the patient's vasculature such that an ablation device may be passed therethrough and positioned to ablate arrhythmia-causing cardiac tissue. The introducer catheter itself may be advanced over a guide wire.

Generally, it is known that the introducer catheter must have an overall diameter small enough to negotiate blood vessels while retaining an inner diameter (or "bore size") large enough to accommodate the ablation device therethrough. Furthermore, since the path within the patient is often long and tortuous, steering forces must be transmitted over relatively great distances. Accordingly, it is desirable for the introducer catheter to have sufficient axial strength to be pushed through the patient's vasculature via a force applied at its proximal end ("pushability"). It is also desirable for the introducer catheter to transmit a torque applied at the proximal end to the distal end ("torqueability"). An introducer catheter should also have sufficient flexibility to substantially conform to the patient's vasculature and yet resist kinking as it does so. One of ordinary skill in the art will recognize that these various characteristics are often in tension with one another, with improvements in one requiring compromises in others. For example, increasing the bore size of an introducer catheter having a given overall diameter requires utilizing a thinner wall. A thin-walled introducer, however, is more likely to collapse upon itself when a torque is applied at its proximal end.

To improve pushability, torqueability, flexibility, and kink resistance, many extant introducer catheters utilize one or more reinforcing layers in their construction. For example, the guiding catheter disclosed in U.S. Pat. No. 4,817,613 to Jaraczewski et al. ("Jaraczewski") includes a pair of braided torque transmitting layers sandwiched between a flexible tubular member and a flexible plastic casing applied as a viscous material and subsequently cured. Jaraczewski also teaches, however, that to a certain degree, flexibility comes at the expense of torqueability. Further, depending on the thickness of the torque transfer layers, they may increase the wall thickness, thereby either increasing the overall diameter of the introducer catheter for a given bore size or decreasing the bore size for a given overall diameter.

Many extant large bore introducers (i.e., an introducer catheter with bore size of greater than about 6 French), in order to find a suitable balance of pushability, torqueability, flexibility, and kink resistance, have outer layers that are relatively stiff, which compromises torqueability, kink resistance, and flexibility for pushability.

BRIEF SUMMARY OF THE INVENTION

Embodiments of the present invention provide a catheter, particularly an introducer catheter, having good pushability, torqueability, flexibility, and kink resistance, while retaining a large bore size for a given overall diameter. In specific embodiments, an introducer catheter with good pushability, torqueability, flexibility, and kink resistance has a bore size of at least about 6 French and an overall diameter suitable for use in cardiac diagnostic and therapeutic procedures. The invention further provides a method of constructing a catheter or introducer catheter that does not require compromising some of the characteristics of pushability, torqueability, flexibility, and kink resistance for others of those characteristics.

Disclosed herein is an introducer catheter having a distal end and a proximal end, including: a polymeric inner liner having a substantially cylindrical distal section, a substantially cylindrical proximal section, and a frusto-conical intermediate section between the distal section and the proximal section; a torque transfer layer surrounding at least a portion of the inner liner; and an outer sheath of a melt-processable polymer formed over the torque transfer layer. The inner liner defines a lumen, which may desirably have a diameter of at least about 12 French.

In some embodiments, the distal section of the inner liner defines a distal section of the lumen and the proximal section of the inner liner defines a proximal section of the lumen, and the diameter of the distal section of the lumen is smaller than the diameter of the proximal section of the lumen. For example, the diameter of the proximal section of the lumen may be between about 0.004" and about 0.005" greater than the diameter of the distal section of the lumen. As another example, the diameter of the distal section of the lumen may be about 12.5 French and the diameter of the proximal section of the lumen may be about 14 French. Typically, the slope of the frusto-conical intermediate section is between about 4 degrees and about 6 degrees, more preferably about 5 degrees.

Optionally, the torque transfer layer includes at least two flat wires braided into a wire mesh. A braid density of the torque transfer layer may vary along a length of the introducer catheter, such as being higher adjacent the intermediate section of the inner liner than elsewhere along the length of the introducer catheter.

Optionally, the distal end of the introducer catheter may be shaped in a preset curvature.

Also disclosed herein is a method of manufacturing an introducer catheter having a distal end and a proximal end. The method generally includes the steps of: forming a polymeric inner liner about a mandrel having an outer diameter that varies along a length of the mandrel, wherein the mandrel has a substantially cylindrical proximal section, a substantially cylindrical distal section, and a frusto-conical transition section between the proximal section and the distal section; forming a torque transfer layer over at least a portion of the inner liner, the torque transfer layer including a plurality of flat wires braided into a wire mesh; forming an outer sheath about the torque transfer layer, the outer sheath comprising a melt-processable polymer; applying energy to the outer sheath to bond the outer sheath to the torque transfer layer and the inner liner; and removing the mandrel, thereby creating a lumen in the introducer catheter, the lumen having a proximal section having a first diameter, a distal section having a second diameter less than the first diameter, and a frusto-conical transition section between the proximal section and the distal section. Optionally, the method further includes the step of forming the distal end of the introducer catheter into a preset curvature.

In another aspect of the invention, an introducer catheter having a distal end and a proximal end includes: a tubular polymeric inner liner having a lumen diameter of at least about 8 French; a torque transfer layer surrounding at least a portion of the inner liner, the torque transfer layer comprising at least two flat wires braided into a wire mesh; and an outer sheath of a melt-processable polymer formed over the torque transfer layer, wherein the outer sheath includes a distal segment and a proximal segment, the proximal segment having a higher durometer than the distal segment, and wherein the distal end of the introducer catheter is formed into a preset curvature.

The distal segment may include a frusto-conical tip segment and a substantially cylindrical intermediate segment positioned between the tip segment and the proximal segment, with the intermediate segment having a durometer that is intermediate to the tip segment and the proximal segment.

It is desirable for the outer diameter of the outer sheath to be less than about 11 French, more preferably less than about 10 French.

A radius of the preset curvature is preferably between about 0.8" and about 1.2", and an arc of the preset curvature is preferably between about 25 degrees and about 45 degrees. More preferably, the radius of the preset curvature is between about 0.9" and about 1.1" and the arc of the preset curvature is between about 30 degrees and about 40 degrees. Most preferably, the radius of the preset curvature is about 1.0" and the arc of the preset curvature is about 35 degrees.

In some embodiments, the introducer catheter further includes a flared transition section proximate the proximal end, the lumen diameter of the inner liner proximate of the flared transition section being larger than the lumen diameter of the inner liner distal of the flared transition section. For example, the flared transition section may be a frusto-conical transition section. The lumen diameter of the inner liner proximal of the flared transition section is preferably between about 0.004" and about 0.005" greater than the lumen diameter of the inner liner distal of the flared transition section.

In still another aspect, the present invention provides a method of manufacturing an introducer catheter having a distal end and a proximal end, generally including the following steps: forming a tubular polymeric inner liner about a mandrel, the mandrel having an outer diameter of at least about 8 French; forming a torque transfer layer over at least a portion of the inner liner, the torque transfer layer including a plurality of flat wires braided into a wire mesh; forming an outer sheath about the torque transfer layer, the outer sheath including at least a distal segment and a proximal segment, wherein each of the distal segment and the proximal segment comprises a melt-processable polymer, and wherein a hardness of the proximal segment is greater than a hardness of the distal segment; heating the inner liner, the torque transfer layer, and the outer sheath to a temperature sufficient to bond the outer sheath to the torque transfer layer and the inner liner; forming the distal end of the introducer catheter into a preset curvature; and removing the mandrel.

The step of forming an outer sheath about the torque transfer layer may include abutting the distal segment of the outer sheath and the proximal segment of the outer sheath such that the distal segment of the outer sheath bonds to the proximal segment of the outer sheath during the heating step. Alternatively, the step of forming an outer sheath about the torque transfer layer may include overlapping the distal segment of the outer sheath and the proximal segment of the inner sheath such that the distal segment of the outer sheath bonds to the proximal segment of the outer sheath during the heating step. In still other embodiments, the step of forming an outer sheath about the torque transfer layer may include extruding the outer sheath about the torque transfer layer such that the melt-processable polymer of the outer sheath occupies a plurality of voids of the wire mesh in the torque transfer layer.

Of course, the distal segment of the outer sheath may include a tip segment and an intermediate segment positioned between the tip segment and the proximal segment of the outer sheath. The tip segment may be a frusto-conical segment.

The foregoing and other aspects, features, details, utilities, and advantages of the present invention will be apparent from reading the following description and claims, and from reviewing the accompanying drawings.

DETAILED DESCRIPTION OF THE INVENTION

The present invention provides a catheter and a large bore introducer catheter suitable for use in the human vasculature for known medical procedures, such as cardiac ablation. For purposes of description, the present invention will be described in connection with a flat wire guided, or steerable, introducer catheter. It is contemplated, however, that the described features may be incorporated into any number of catheters or introducer catheters as would be appreciated by one of ordinary skill in the art. The large bore introducer catheter is comprised of a combination of components and manufactured by either a reflow process or an extrusion process, which provide the surprising benefits of allowing for introducer catheters having an internal diameter of at least about 6 French while maintaining the desirable improved properties of pushability, torquability, and flexibility, for outer diameters of sufficient size for navigation of cardiac vasculature.

Figure 1:
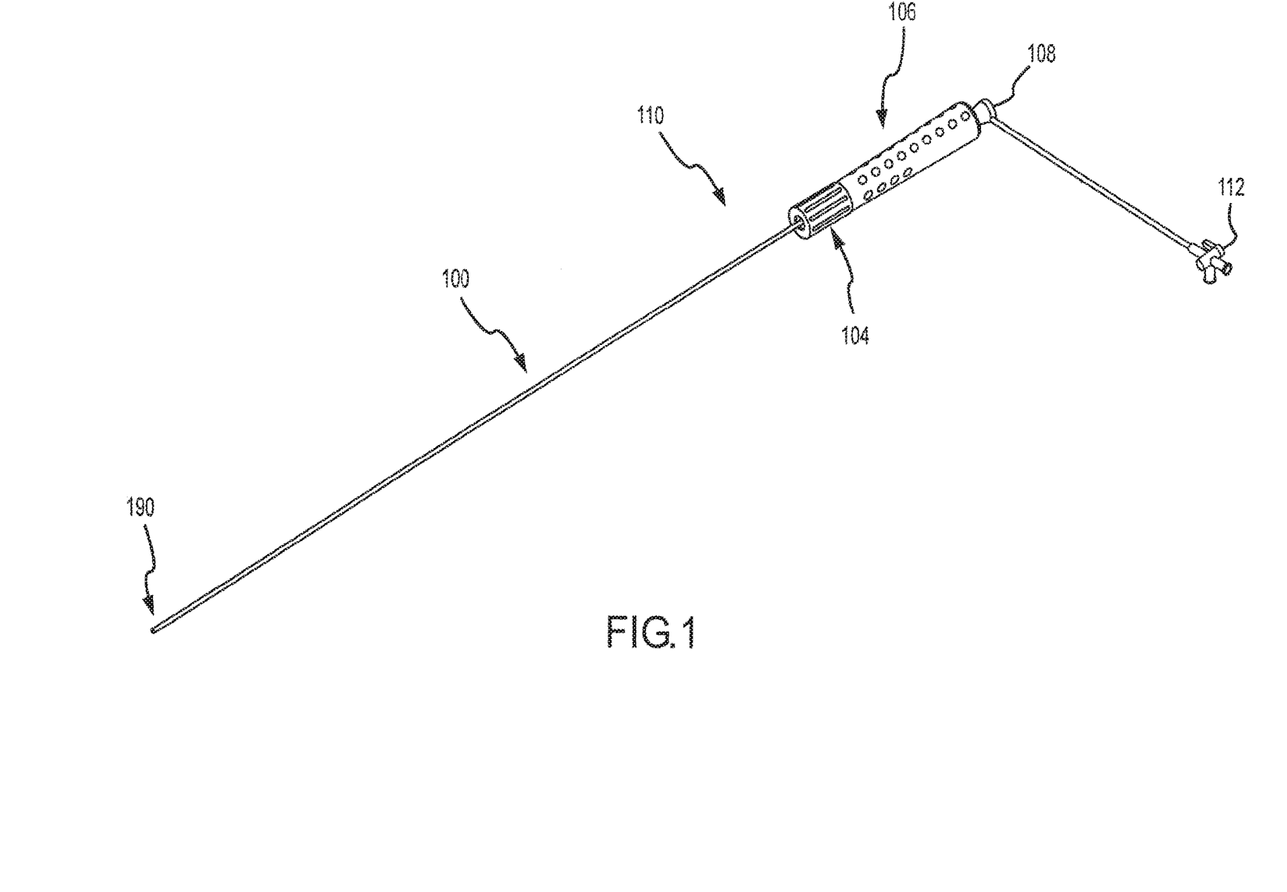
FIG. 1 is a perspective view of an introducer assembly in accordance with one embodiment of the present invention.

FIG. 1 is a perspective view of an introducer assembly 110 according to one embodiment of the present invention comprising an introducer catheter 100 having a distal end 190 and a proximal end 104. The introducer catheter 100 may be operably connected to a handle assembly 106 which assists in guiding or steering the introducer during procedures. The introducer assembly 110 further includes a hub 108 operably connected to an inner lumen (not shown) within the handle assembly 106 for insertion or delivery of catheter assemblies, fluids, or any other devices known to those of ordinary skill in the art. Optionally, the introducer assembly 110 further includes a valve 112 operably connected to the hub 108.

Figure 2:
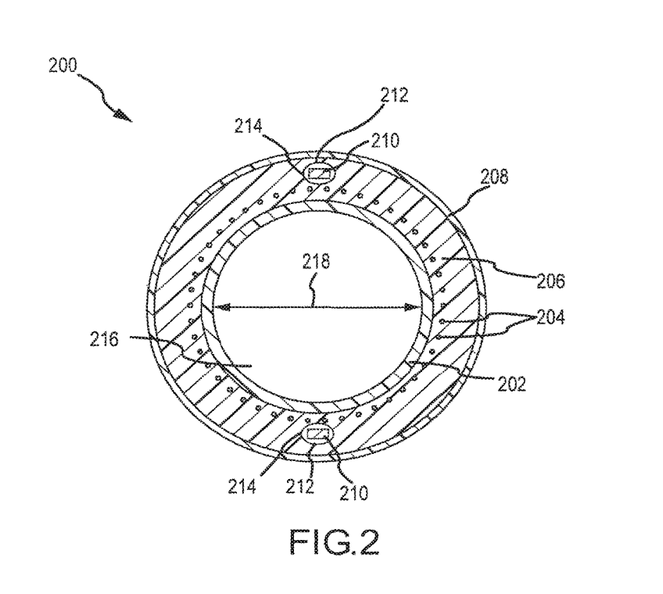
FIG. 2 is a cross-sectional view of a steerable, large bore introducer catheter in accordance with an embodiment of the present invention.

FIG. 2 depicts a cross-sectional view of an introducer catheter 200 in accordance with one embodiment of the present invention. The introducer catheter 200 is comprised of a tubular polymeric inner liner 202, a torque transfer layer 204, an outer sheath 206 comprised of a melt-processable polymer, and a heat shrink layer 208. In the instance where the introducer is a steerable introducer, the introducer catheter 200 further includes at least one flat wire 210 disposed longitudinally along the length of the introducer catheter 200. For purposes of this invention, a "flat wire" refers to a wire that is characterized by a cross-section that, when measured along two orthogonal axes, is substantially flat. A flat wire typically has a rectangular cross section, though the cross section need not be perfectly rectangular. For example, the present invention contemplates that a cross section of the flat wire may be oval, provided that the overall cross section is generally flat. As the term is used herein, a wire may be properly characterized as a flat wire if it has a cross section that is measured x in one direction and at least 2× in a second direction generally orthogonal to the first direction. A wire whose cross section is substantially I-shaped may also be a flat wire if, generally, its height is substantially greater than its width at its widest measurement. One of ordinary skill will appreciate that a flat wire may be defined in the context of the overall teachings of this application.

The at least one flat wire 210 may be further encased inside another polymeric tubular member 212 forming a lumen 214 for housing the flat wire 210. The introducer catheter according to this embodiment is manufactured by a reflow bonding process in which the components are individually fed over a mandrel as discussed in more detail below.

The inner liner 202 is preferably a polymeric material, such as polytetrafluoroethylene (PTFE) or etched PTFE. The inner liner 202 may also be made of other melt processable polymers, including, without limitation, polyether block amides, nylon and other thermoplastic elastomers. Once such elastomer is Pebax® made by Arkema, Inc. Pebax of various durometers may also be used, including without limitation, Pebax 30D to Pebax 70D. In a preferred embodiment, the inner liner 202 is made of a material with a melting temperature higher than the outer sheath 206 such that the inner liner 202 will withstand the melt processing of the outer sheath 206.

Inner liner 202 defines a lumen 216 therethrough, preferably having a diameter 218 of at least about 6 French, more preferably of at least about 7 French, and most preferably of between about 10 French and about 24 French. However, in some embodiments of the invention, it is contemplated that lumen 216 may have a diameter 218 of up to about 32 French or more, such as between about 7 French and about 32 French.

A torque transfer layer 204 is preferably disposed between the inner liner 202 and the heat shrink layer 208, more preferably between the outer sheath 206 and the inner liner 202. In the instance where the introducer is a steerable introducer utilizing, for example, at least one longitudinal wire 210, the torque transfer layer 204 may be disposed between either the inner layer 202 and the outer sheath 206 or the outer sheath 206 and the heat shrink layer 208. The torque transfer layer 204 may be made of stainless steel (304 or 316) wire or other acceptable materials known to those of ordinary skill in the art.

The torque transfer layer 204 is preferably formed of a braided wire assembly comprised of flat wires, preferably stainless steel wires including, for example, high tensile stainless steel wires. The torque transfer layer 204 may be formed in any number of known braid patterns, including one-over-one (involving at least two wires) or two-over-two (involving at least four wires) crossover patterns. For lumen diameters of at least about 6 French, braided flat wires of at least about 0.003" thick by at least about 0.007" wide, which heretofore were not used to form a wire mesh for the torque transfer layer, have produced surprisingly good results of increased pushability, torqueability, flexibility, and kink resistance over non-flat wires and smaller flat wires. In general, the individual wires have a ratio of width to the thickness of at least about 2:1, including, for example, 2:1 to 5:1. Flat wires of about 0.004" thick by about 0.012" wide and of about 0.004" thick by about 0.020" wide have also been braided with success to form torque transfer layers of superior performance. Of course, other wire sizes, such as at least about 0.002" thick by about 0.006" wide, may also be utilized without departing from the spirit and scope of the present invention.

The braid density, commonly measured in pixels per inch ("PPI"), is typically between about 5 and about 100, and will depend on the size of the flat wires as well as the size of the catheter. For flat wires of at least about 0.003" thick by about 0.007" wide and a catheter having an inner lumen of at least about 6 French, the braid density is preferably between about 10 PPI and about 90 PPI, more preferably between about 10 PPI and about 55 PPI. For example, the braid density for flat wires of about 0.003" thick by about 0.007" wide is preferably between about 20 PPI and about 90 PPI, more preferably between about 35 PPI and about 55 PPI for an inner lumen of at least 6 French, and most preferably between about 35 PPI and about 45 PPI for an inner lumen of at least about 10 French. The braid density for flat wires of about 0.004" thick by about 0.012" wide is preferably between about 15 PPI and about 70 PPI, and more preferably between about 15 PPI and about 22 PPI for an inner lumen of at least about 6 French. The braid density for flat wires of about 0.004" thick by about 0.020" wide is preferably between about 5 PPI and about 50 PPI, and more preferably between about 10 PPI and about 20 PPI for an inner lumen of at least about 6 French, and most preferably between about 10 PPI and about 20 PPI for an inner lumen of at least about 16 French.

Alternatively, the torque transfer layer 204 may utilize a varying braid density construction along the length of the introducer catheter 200. For example, the torque transfer layer may be characterized by a first braid density at the proximal end of the introducer catheter 200 and then transition to one or more braid densities as the torque transfer layer 204 approaches the distal end of the introducer catheter 200; the braid density of the distal end may be greater or less than the braid density at the proximal end. In a specific example, the braid density at the proximal end is about 50 PPI and the braid density at the distal end is about 10 PPI. In another embodiment, the braid density at the distal end is about 20-35% of the braid density at the proximal end.

The torque transfer layer 204 may be formed separately on a disposable core and subsequently slipped around the inner liner 202. One or more portions of the torque transfer layer 204 may be heat tempered and cooled before incorporation into the introducer body 200 through methods that are known to those of ordinary skill. The action of heat tempering may help to release the stress on the wire and help reduce radial forces. It is also contemplated that torque transfer layer 204 may be braided directly on the inner liner 202.

A particularly preferred torque transfer layer 204 is comprised of 0.003" by 0.007" 304 stainless steel wires at 35 PPI for an inner lumen of 6-10 French. Another preferred torque transfer layer 204 is comprised of 0.004" by 0.012" 304 stainless steel wires at 22 PPI for an inner lumen of 12 French. Yet another preferred torque transfer layer 204 is comprised of 0.004" by 0.020" 304 stainless steel wires at 13 PPI for an inner lumen of 16 French. These particularly preferred torque transfer layers may be manufactured on a commercially available horizontal braid machine set at 225 rpm utilizing a commercially available mandrel. Other suitable methods of manufacturing the torque transfer layer 204 will be apparent to those of ordinary skill in the art.

Figure 6:
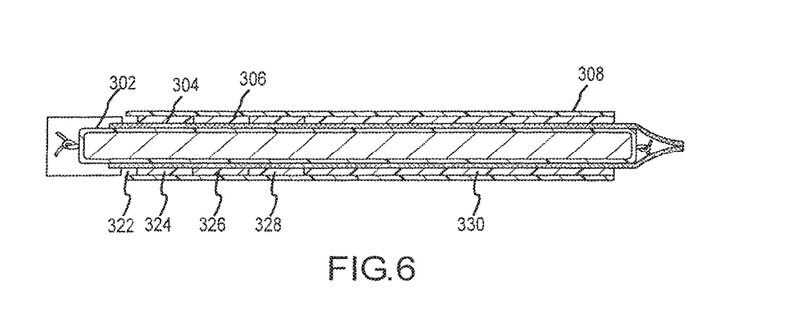
FIG. 6 depicts an outer sheath of varying components disposed over a torque transfer layer in accordance with a preferred method of manufacture.

The outer sheath 206 is preferably either an extruded Pebax or PTFE tubing. The melt-processable polymer of the outer sheath 206 occupies a plurality of voids of the wire mesh in the torque transfer layer 204. The outer sheath 206 may also be made of other melt processable polymers, including, without limitation, etched PTFE, polyether block amides, nylon and other thermoplastic elastomers, at varying durometers. The outer sheath 206 may also comprise more than one layer, including, for example, two or more tubes of a melt processable polymer. Alternatively, as shown in FIG. 6, the outer sheath 306 may be comprised of varying segments 322, 324, 326, 328, 330 differing in hardness and/or material along the length of the introducer 300 and being reflow bonded together. This may be accomplished by layering or by placing annular rings of differing materials along the length of the introducer 300. Varying the sheath composition in this manner provides the additional benefit of adjusting flexibility, torquability, and pushability at various points along the introducer 300.

Figure 10:
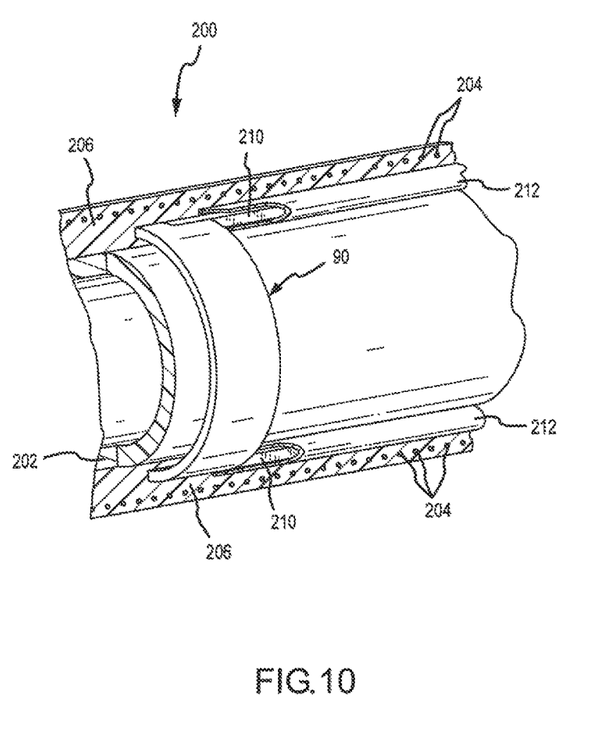
FIG. 10 is a perspective view of a steerable introducer catheter in accordance with an embodiment of the present invention, cut away to show details of the steering ring.

In embodiments where the introducer is a steerable introducer (as shown in FIG. 2), at least one flat wire 210 is provided, preferably extending along substantially the entire length of the introducer. The flat wire 210 is preferably composed of stainless steel and is preferably about 0.002"× about 0.006", and more preferably about 0.004"× about 0.012" or 0.016". The flat wire may be selected such that the ratio of the width to thickness is at least about 2:1. In one embodiment, at least a portion of the flat wire is encased inside a preformed tube 212 before placement along the inner liner 202 to form a flat lumen 214. The preformed tube 212 need not be the same shape as the cross section of the flat wire, but instead, may be round, oval, rectangular, or another like shape. Preferably, the preformed tube 212 has a cross section that is not the same shape as a cross section of the flat wire 210, in order to facilitate movement of the flat wire in the preformed tube. The preformed tube may be formed of PTFE, etched PTFE, polyether block amides (such as Pebax), nylon, other thermoplastic elastomers, or any other known material to one of ordinary skill in the art. Preferably, the preformed tube 212 has a higher melting point than the outer sheath 206 so that the preformed tube 212 will not melt when the introducer catheter 200 is subjected to melt processing. In alternative embodiments the flat wire 210 may be covered with lubricious materials (not shown) before placement, including silicone and other lubricious materials. Alternatively, the flat wire 210 may also be coated with a lubricious layer to promote slideability, and it is also contemplated that the flat wire 210 may be manufactured with a smooth surface to promote slideability. While stainless steel is a preferred material to compose the flat wire 210, other materials may be used, including, without limitation, materials that are used for conventional round pull wires. More than one flat wire 210 may also be used, and in such cases, each such flat wire 210 may be encased inside its own flexible tube 212. Preferably, as shown in FIG. 2, a pair of flat wires 210 are used that are spaced at 180 degrees apart. The flat wires 210 are preferably connected to at least one steering ring 90 typically located near the distal end of the introducer (see, e.g., FIG. 10). The proximal ends of the flat wires 210 are then operably connected to a steering mechanism (not shown) allowing for manipulation, or steering, of the introducer catheter 200 during use. FIG. 10 shows a cutaway view of the introducer catheter 200 according to the present invention highlighting the steering ring 90 and its connection to the pull wires 210.

Figure 3:
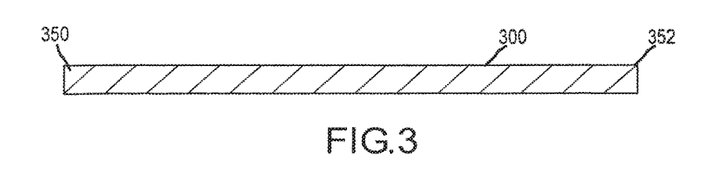
FIG. 3 depicts a reflow mandrel assembly used in the method of manufacturing introducer catheters in accordance with the present invention.
Figure 4:
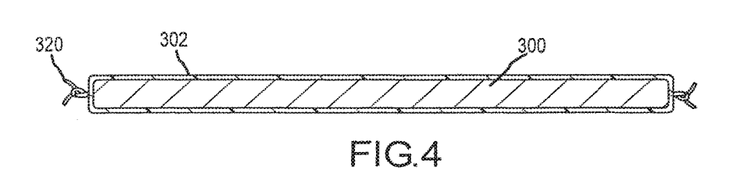
FIG. 4 depicts an inner layer disposed over a reflow mandrel assembly in accordance with a preferred method of manufacture.

The basic method of manufacture according to an embodiment of the present invention will be described in reference to FIGS. 3-9. As the various components are assembled, the introducer components will be collectively referred to as an introducer. As depicted in FIGS. 3-9, a mandrel 300, which is preferably round in cross-section and preferably from about 6 inches to about 4 feet in length, is provided. As depicted in FIG. 3, the mandrel 300 has a distal end 350 and a proximal end 352. As depicted in FIG. 4, an inner liner 302 is placed on the mandrel 300. The inner liner 302 is fed on to the mandrel 302 and is then knotted on one end 320, or both ends.

Figure 5:
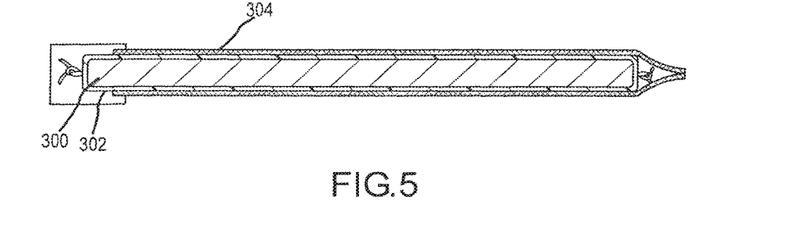
FIG. 5 depicts a torque transfer layer disposed over an inner layer in accordance with a preferred method of manufacture.

As depicted in FIG. 5, a torque transfer layer 304 is then placed over the inner liner 302. In the case of a steerable introducer catheter, the flat wire assembly (not shown) may then be placed over the torque transfer layer 304. Alternatively, the flat wire assembly may be placed over an outer sheath 306. Another sheath layer (not shown) may additionally be placed over the flat wire assembly. The torque transfer layer terminates proximally of the distal end of the catheter.

Next, as depicted in FIG. 6, an outer sheath 306 is placed over the torque transfer layer 304 and may be made of either single or multiple sections of tubing that are either butted together or overlapped with each other. The multiple segments, or layers, of sheath material may be any length and/or hardness (durometer) allowing for flexibility of design. FIG. 6 identifies a plurality of segments, 322, 324, 326, 328 and 330. In this embodiment, the proximal end 330 of the outer sheath 306 may be made of a material such as nylon, and the remainder of the introducer may be made of one or more Pebax materials. The lengths of the various segments may vary, but preferably, the durometer hardness levels will decrease as the outer sheath 306 approaches its distal end. For example, a nylon base may then be followed by one or more of the following Pebax segments: 70D Pebax; 60D Pebax; 55D Pebax; 40D Pebax; 35D Pebax; 30D Pebax. The introducer shaft may also use one or more blends of the foregoing Pebax materials, including, for example, 70D/60D Pebax blend made by co-extrusion, or a 40D/35D Pebax blend made by co-extrusion. Preferably, the various components of the outer sheath 306 according to this embodiment will be reflowed together during manufacturing. The proximal end of the shaft is preferably the longest segment, and more distal segments may preferably vary between 0.25" to 6", and more preferably from 0.25" to about 3". Preferably, the hardness levels of the segments and the lengths of the segments may be adjusted for specific applications, and preferably, the distal end may have the lowest durometer levels of all segments. The shaft segments may be selected to improve flexibility, torquability, and pushability for the specific application, as appreciated by one of ordinary skill in the art. Alternatively, the catheter may be formed by placing a thin inner jacket or layer (e.g., PTFE layer) onto a mandrel (e.g., stainless steel mandrel) or extruding a thin inner jacket or layer (e.g., Pebax layer) onto an extrusion mandrel (e.g., acetal mandrel), forming a torque transfer layer over the inner layer, and extruding an outer jacket or sheath (e.g., Pebax jacket) over the torque transfer layer.

Lastly, a heat shrink layer 308 is placed over the assembled introducer assembly prior to reflow lamination. The heat shrink layer 308 is preferably a fluoropolymer or polyolefin material, such as FEP, or other suitable material as appreciated by one of ordinary skill in the art.

After assembly of the various components, the introducer assembly 300 is subjected to a reflow lamination process. FIG. 2 depicts a cross sectional view of the introducer assembly after this reflow process. Introducer assembly 200 may be laminated by heating the assembly until the material comprising the outer sheath 206 flows and redistributes around the circumference. Preferably, the heat shrink layer 208 has a higher melt temperature than the outer sheath 206, and during the melt process, the heat shrink layer 208 retains its tubular shape and forces the liquefied sheath layer material 206 into the torque transfer layer 204 and into contact with the flat wires 210/preformed tubes 212 (if present) and the inner liner 202. The introducer assembly 200 may then be cooled. The mandrel is preferably left in place during the cooling process as it helps the introducer assembly to retain its inner lumen of at least about 6 French. The heat shrink layer 208 may be left on the introducer assembly 200, or optionally removed. If the heat shrink layer 208 is removed, the outer sheath 206 becomes the outside layer of the introducer catheter 200.

Figure 7:
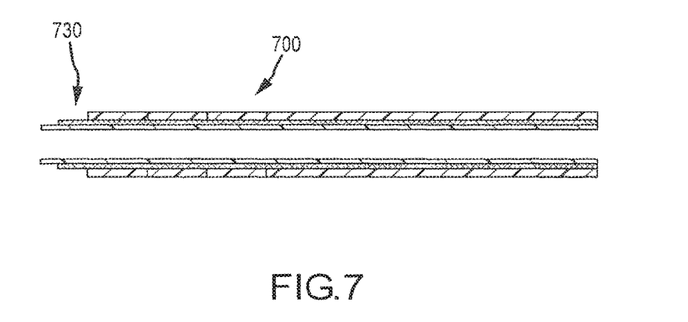
FIG. 7 depicts the components of an introducer catheter assembled over a reflow mandrel assembly having a distal configuration for a tip assembly.
Figure 8:
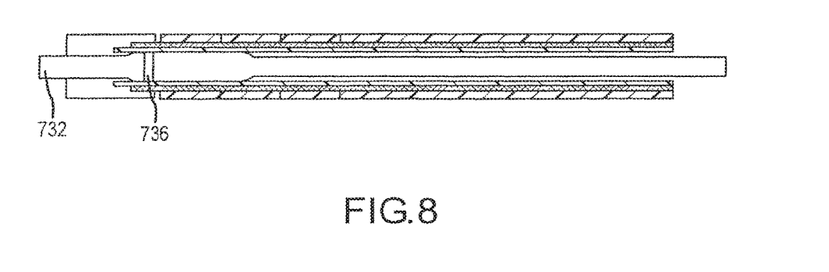
FIG. 8 depicts a tip component, having a radiopaque marker, attached to the distal end of the introducer catheter depicted in FIG. 7.
Figure 9:
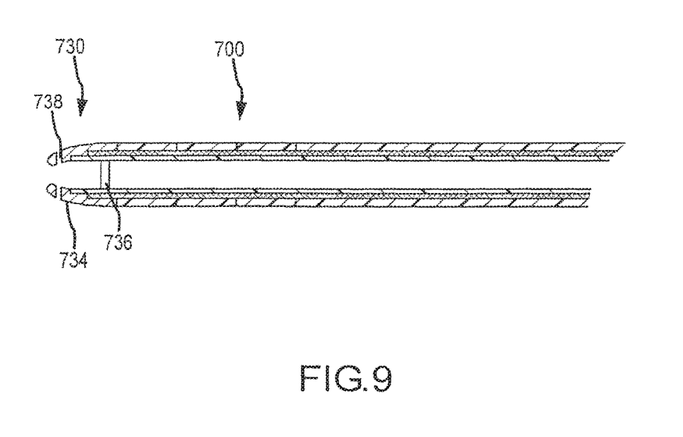
FIG. 9 depicts another tip component, having a radiopaque marker, attached to the distal end of the introducer catheter depicted in FIG. 7.

Additionally, as shown in FIGS. 7-9, the present invention contemplates the inclusion of a tip assembly for use in medical procedures, such as an atraumatic tip, including, for example, a radiopaque material contained therein for location of the tip during use. For example, FIGS. 7-9 depict a cross section of an introducer catheter 700 having a distal portion 730 configured to accept a tip assembly 732 or 734. In both examples, the tip 732 or 734 includes a ring 736, e.g., a radiopaque marker, for location of the tip 732 or 734 during use. Additionally, FIG. 9 further includes a tip assembly 734 configured with a plurality of port holes 738 for delivery of, for example, irrigation fluid. The tip assembly may further be configured with ablation electrodes (not shown) operably connected to a power supply (not shown), for use in cardiac ablation procedures.

Figure 11:
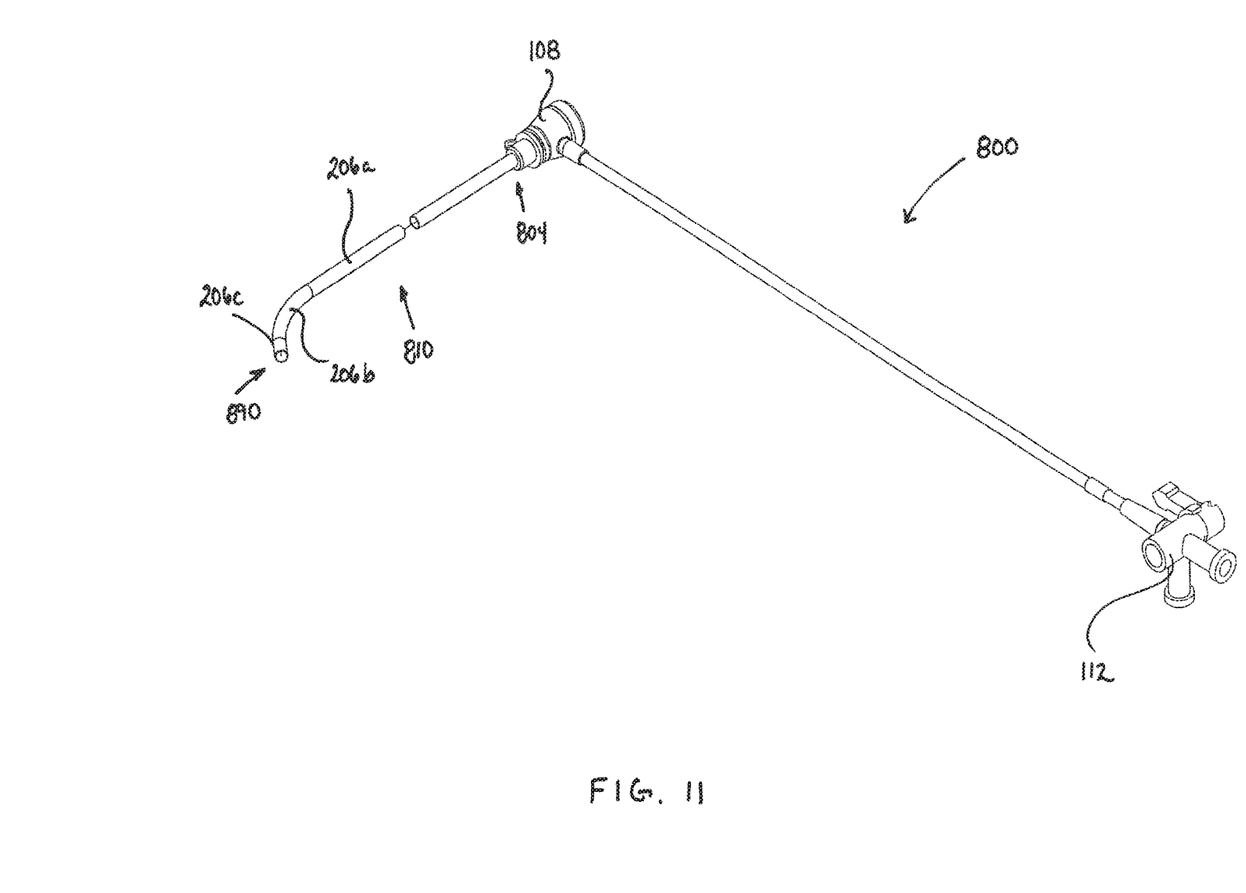
FIG. 11 is a perspective view of an introducer assembly in accordance with another embodiment of the present invention.
Figure 12:
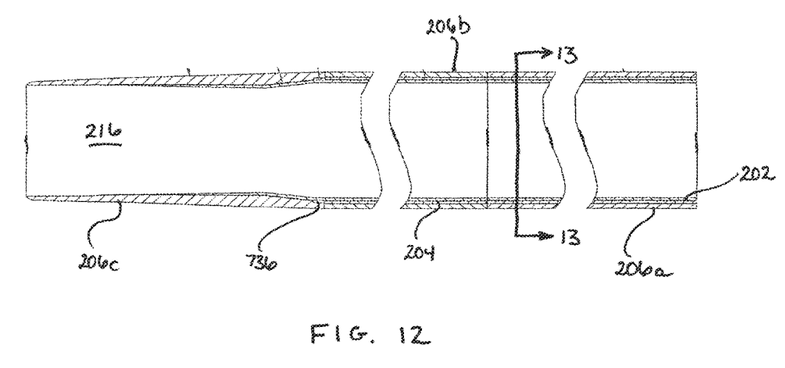
FIG. 12 is a sectional view of the introducer assembly of FIG. 11.
Figure 13:
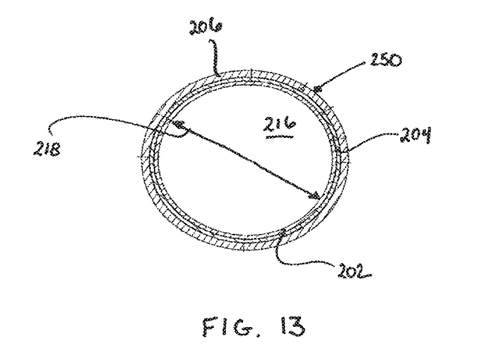
FIG. 13 is a cross-sectional view taken along line 13-13 in FIG. 12.

Another embodiment of the present invention is depicted as introducer assembly 800 in FIGS. 11-13. Introducer assembly 800 includes an introducer catheter 810 having a distal end 890 and a proximal end 804. Similar to the embodiment illustrated in FIG. 1, introducer catheter 810 may be operably coupled to a hub 108, which is operably connected to inner lumen 216 (FIGS. 12 and 13) for insertion or delivery of catheter assemblies, fluids, or any other devices known to those of ordinary skill in the art. Hub 108 may in turn be operably coupled to a valve 112.

As shown in FIG. 12, introducer catheter 810 includes inner liner 202, torque transfer layer 204, and outer sheath 206, as well as radiopaque marker 736, as described in detail above. Torque transfer layer 204 may terminate proximally of distal end 890 of introducer catheter 810 as shown, or may extend substantially the entire length of introducer catheter 810. Inner liner 202 may also terminate proximally of distal end 890 of introducer catheter 810 as shown or extend substantially the entire length thereof.

Preferably, the inner diameter 218 (FIG. 13) of inner liner 202 is at least about 8 French, while the outer diameter 250 of outer sheath 206 is less than about 11 French, more preferably less than about 10 French. Of course, the inner and outer diameters of introducer catheter 810 may be varied by one of ordinary skill in the art in accordance with the principles disclosed herein in order to adapt introducer catheter 810 for various surgical applications, therapeutic applications, diagnostic applications, and the like.

Outer sheath 206 includes a proximal segment 206a, an intermediate segment 206b, and a tip segment 206c. Intermediate segment 206b and tip segment 206c may be collectively referred to as a "distal segment" to distinguish them from proximal segment 206a. In some embodiments of the invention, tip segment 206c may be frusto-conical (e.g., as shown in FIG. 12), in order to facilitate insertion of introducer catheter 810 into a patient and navigation of introducer catheter 810 through the patient's vasculature, while intermediate segment 206b and proximal segment 206a are substantially cylindrical. It is contemplated, however, that tip segment 206c may also be substantially cylindrical.

As described above, segments 206a, 206b, and 206c may vary in length, for example with proximal segment 206a being longer than intermediate segment 206b, which is in turn longer than tip segment 206c. In one embodiment of the invention, proximal segment 206a may be about 23.5 inches long, intermediate segment 206b may be about 1.5 inches long, and tip segment 206c may be about 0.25 inches long.

Similarly, segments 206a, 206b, and 206c vary in durometer, with proximal segment 206a having a higher durometer than the distal segment. In particular, proximal segment 206a has a higher durometer than intermediate segment 206b, which in turn has a higher durometer than tip segment 206c. For example, proximal segment 206a may have a durometer of 72D, intermediate segment 206b may have a durometer of about 55D, and tip segment 206c may have a durometer of about 35D.

As best seen in FIG. 11, distal end 890 of introducer 810 may be shaped into a preset curvature. One preferred preset curvature has a radius of between about 0.8 inches and about 1.2 inches, more preferably between about 0.9 inches and about 1.1 inches, and most preferably of about 1 inch, while the arc of the curvature is preferably between about 25 degrees and about 45 degrees, more preferably between about 30 degrees and 40 degrees, and most preferably about 35 degrees. It is contemplated, however, that other preset curvatures may be utilized without departing from the spirit and scope of the present invention. For example, distal end 890 of introducer catheter 810 may be shaped into any desired curvature for a particular application of introducer catheter 810, for example cardiac ablation.

Figure 14:
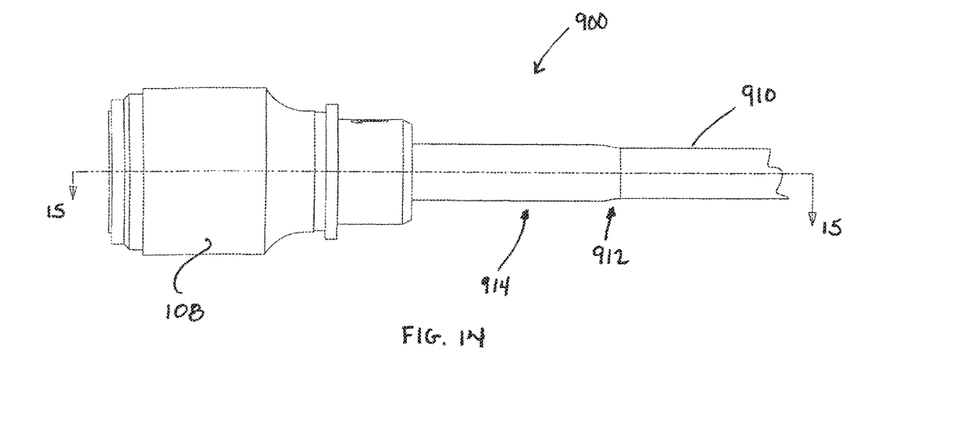
FIG. 14 illustrates the proximal end of an introducer catheter including a flared transition section.
Figure 15:
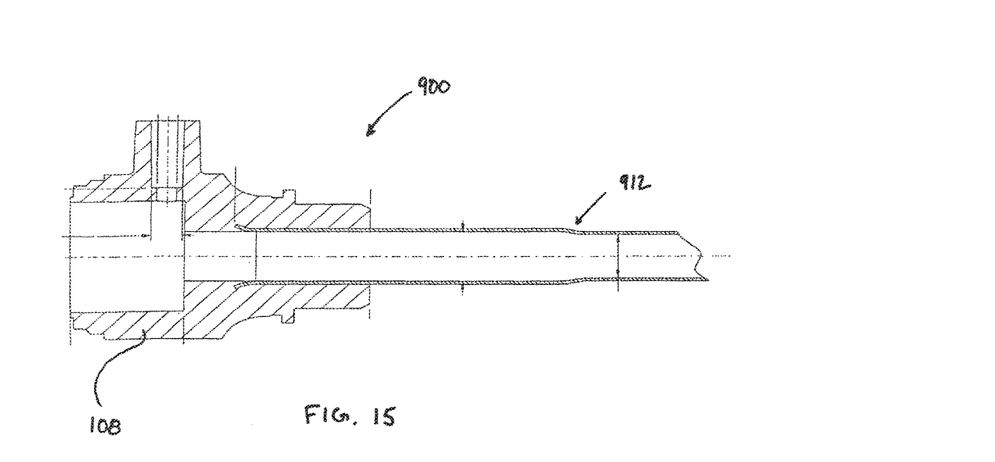
FIG. 15 is a cross-sectional view taken along line 15-15 in FIG. 14.

FIGS. 14 and 15 illustrate an introducer assembly 900 according to another embodiment of the present invention. In particular, FIGS. 14 and 15 illustrate an introducer catheter 910 including a flared transition section 912 at its proximal end 914 (e.g., proximate where introducer catheter 910 is coupled to hub 108). Such a transition section is desirable where the introducer catheter 910 is as large as at least about 12 French, but may of course be practiced in connection with catheters and introducer catheters of other sizes without departing from the spirit and scope of the present invention.

As illustrated to good advantage in FIGS. 14 and 15, flared transition section 912 may be a frusto-conical section that permits a gradual reduction in the lumen diameter of introducer catheter 910. The lumen diameter of introducer catheter 910 will be larger proximal of transition section 912 than distal of transition section 912. Typically, the lumen diameter of introducer catheter 910 will be between about 0.004" and about 0.005" larger proximal of transition section 912 than distal of transition section 912, though other deltas are within the scope of the present teachings. Preferably, the slope of the transition section 912 is between about 4 degrees and about 6 degrees, and more preferably is about 5 degrees. Of course, other angles may be utilized consistent with the present teachings.

The smooth (or funnel-like) transition facilitated by flared transition section 912 advantageously permits introduction of larger medical devices into the patient without such devices getting "hung up" within the hub and without increasing the outer diameter of the section of the introducer catheter that is introduced into the patient. This may be particularly desirable, for example, where a large inflatable member, such as a 30 mm balloon, is to be introduced through introducer catheter 910.

Although several embodiments of this invention have been described above with a certain degree of particularity, those skilled in the art could make numerous alterations to the disclosed embodiments without departing from the scope of this invention. For example, one of ordinary skill in the art will appreciate that the features and principles disclosed herein could be practiced in various combinations depending on the needs of a particular procedure (e.g., an introducer catheter including both a flared transition section and a curved distal end, an introducer catheter including a flared transition section that varies longitudinally in hardness, and the like). One of ordinary skill will also recognize that the teachings herein may be applied to catheters and introducer catheters of varying size, shape, and characteristic (e.g., varying lengths, outer diameters, curvatures, hardnesses, and the like).

In addition, though the invention has been described primarily in connection with braided flat wires, it is contemplated that the torque transfer layer may include one or more non-flat wires (e.g., round wires) and/or one or more helically-wound wires in addition to or as an alternative to braided flat wires. Likewise, materials other than stainless steel (e.g., Kevlar fibers) may be utilized in the torque transfer layer without departing from the scope of the present teachings.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An introducer catheter having a distal end and a proximal end, the introducer catheter comprising:
   a tubular polymeric inner liner having a lumen diameter of at least about 8 French;
   a torque transfer layer surrounding at least a portion of the inner liner, the torque transfer layer comprising at least two flat wires braided into a wire mesh;
   an outer sheath of a melt-processable polymer formed over the torque transfer layer, wherein the outer sheath includes a distal segment and a proximal segment, the proximal segment having a higher durometer than the distal segment; and
   at least one flat pull wire disposed longitudinally between the distal end and the proximal end of the introducer catheter, wherein the at least one flat pull wire is connected to a pull ring,
   wherein the outer sheath is formed over a first tubular member, wherein the first tubular member is external to the torque transfer layer, and wherein the at least one flat pull wire is disposed within the first tubular member.

2. The introducer catheter of claim 1, wherein the outer sheath is formed over a second tubular member, wherein the second tubular member is external to the torque transfer layer, wherein the first and second tubular members are opposite each other in the outer sheath, and wherein a second flat pull wire is disposed within the second tubular member.

3. The introducer catheter of claim 1, wherein the at least one flat pull wire extends along substantially the entire length of the introducer catheter.

4. The introducer catheter according to claim 1, wherein the distal segment comprises a frusto-conical tip segment and a substantially cylindrical intermediate segment positioned between the tip segment and the proximal end, and wherein the intermediate segment has a durometer intermediate to the tip segment and the proximal end.

5. A method of manufacturing an introducer catheter having a distal end and a proximal end, the method comprising:

forming a tubular polymeric inner liner about a mandrel, the mandrel having an outer diameter of at least about 8 French;

forming a torque transfer layer over at least a portion of the inner liner, the torque transfer layer including a plurality of flat wires braided into a wire mesh;

placing a preformed pull wire lumen over the torque transfer layer;

forming an outer sheath about the torque transfer layer, the outer sheath including at least a distal segment and a proximal segment, wherein each of the distal segment and the proximal segment comprises a melt-processable polymer, and wherein a hardness characteristic of the proximal segment is greater than a hardness characteristic of the distal segment, and wherein the melting point of the outer sheath is lower than the melting point of the preformed pull wire lumen;

subjecting the inner liner, the torque transfer layer, and the outer sheath to a reflow lamination process, wherein the outer sheath bonds to the torque transfer layer and the inner liner; and removing the mandrel.

6. The method of claim 5, wherein at least a portion of a flat pull wire is encased within the preformed pull wire lumen.

7. The method according to claim 5, wherein the step of forming an outer sheath about the torque transfer layer comprises abutting the distal segment of the outer sheath and the proximal segment of the outer sheath such that the distal segment of the outer sheath bonds to the proximal segment of the outer sheath during the heating step.

8. The method according to claim 5, wherein the torque transfer layer extends substantially the entire length of the introducer catheter.

9. An introducer catheter having a distal end and a proximal end, the introducer catheter comprising:

a tubular polymeric inner liner having a lumen diameter of at least about 8 French;

a torque transfer layer surrounding at least a portion of the inner liner, the torque transfer layer comprising at least two flat wires braided into a wire mesh;

an outer sheath of a melt-processable polymer formed over the torque transfer layer, wherein the outer sheath includes a distal segment and a proximal segment, the proximal segment having a higher durometer than the distal segment; and at least one flat pull wire disposed longitudinally between the distal end and the proximal end of the introducer catheter, wherein the at least one flat pull wire is connected to a pull ring, wherein the at least one flat pull wire is external to the torque transfer layer and is surrounded by a lumen within the outer sheath.

* * * * *